US007022340B2

(12) United States Patent
Lomryd et al.

(10) Patent No.: US 7,022,340 B2
(45) Date of Patent: *Apr. 4, 2006

(54) PHARMACEUTICAL COMPOSITION AS SOLID DOSAGE FORM AND METHOD FOR MANUFACTURING THEREOF

(75) Inventors: Hakan Lomryd, Malmo (SE); Helena Nicklasson, Malmo (SE); Lars-Erik Olsson, Malmo (SE)

(73) Assignee: Ferring B.V., Hoofddorp (NL)

( * ) Notice: Subject to any disclaimer, the term of this patent is extended or adjusted under 35 U.S.C. 154(b) by 217 days.

This patent is subject to a terminal disclaimer.

(21) Appl. No.: 10/626,857

(22) Filed: Jul. 25, 2003

(65) Prior Publication Data

US 2005/0019392 A1    Jan. 27, 2005

(51) Int. Cl.
*A61K 9/20* (2006.01)
*A61K 9/26* (2006.01)

(52) U.S. Cl. .................. 424/470; 424/464; 424/465

(58) Field of Classification Search ............ 424/464, 424/465, 470
See application file for complete search history.

(56) References Cited

U.S. PATENT DOCUMENTS

| 4,675,188 | A | 6/1987 | Chu |
| 4,820,627 | A | 4/1989 | McGeehan |
| 5,047,398 | A | 9/1991 | Hagstam et al. |
| 2002/0122817 | A1 | 9/2002 | Gabel et al. |
| 2003/0091637 | A1 | 5/2003 | Petereit et al. |
| 2003/0175214 | A1 | 9/2003 | Staniforth et al. |
| 2003/0185764 | A1 | 10/2003 | Staniforth et al. |
| 2004/0220080 | A1* | 11/2004 | Lomryd et al. .......... 514/2 |

FOREIGN PATENT DOCUMENTS

| EP | 0 752 877 B1 | 7/2000 |
| EP | 0 710 122 B1 | 12/2001 |
| EP | 1 255 557 A1 | 11/2002 |
| WO | WO 95/18602 | 7/1995 |
| WO | WO 97/15297 A | 5/1997 |
| WO | WO 97/23485 A1 | 7/1997 |
| WO | WO 00/9423 A | 10/2000 |
| WO | WO 01/78694 A2 | 10/2001 |

(Continued)

OTHER PUBLICATIONS

Robert O. Williams III et al., "Compaction Properties of Microscrystalline Cellulose and Sodium Sulfathiazole in Combination with Talc or Magnesium Stearate", Journal of Pharmaceutical Sciences, vol. 78, No. 12, Dec. 1989, pp. 1025-1034.

(Continued)

*Primary Examiner*—Carlos A. Azpuru
(74) *Attorney, Agent, or Firm*—Foley & Lardner LLP

(57) ABSTRACT

The present invention relates to a novel pharmaceutical composition as a solid dosage form comprising desmopressin as a therapeutically active ingredient, and to a method for manufacturing thereof. The invention relates to a pharmaceutical composition as a solid dosage form comprising desmopressin, or a pharmaceutically acceptable salt thereof, as a therapeutically active ingredient together with a pharmaceutically acceptable excipient, diluent or carrier, or mixture thereof; wherein the pharmaceutical composition is composed of a compressed granulate and contains lubricant in an amount of from 0.05 to less than 0.50 percent by weight of said pharmaceutical composition.

55 Claims, 2 Drawing Sheets

Size distribution of the granulate prepared in example 1

FOREIGN PATENT DOCUMENTS

| WO | WO 01/78695 A2 | 10/2001 |
| WO | WO 01/78696 A2 | 10/2001 |
| WO | WO 01/82906 A1 | 11/2001 |
| WO | WO 02/00197 A1 | 1/2002 |
| WO | WO 03/094886 A2 | 11/2003 |

OTHER PUBLICATIONS

"Pharmaceutical Dosage Forms: Tablets"; vol. 1, pp. 297-298, H.A. Lieberman et al., New York & Basel, 1989.

"Pharmaceutical Dosage Forms: Parenteral Medications", vol. 3, pp. 27-29, H.A. Lieberman et al., New York & Basel, 1990.

"Pharmaceutics—The Science of Dosage Form Design", pp. 625-627, M.E. Aulton et al., Edinburgh, London, Melbourne & New York, 1988.

"Handbook of Pharmaceutical Excipients", Ed. A.H. Kibble, $3^{rd}$ Ed., American Pharmaceutical Assocation, USAS and Pharmaceutical Press UK 2000.

N.A. Armstrong; "Tabletting", Pharmaceutics—The Science of Dosage Form Design, pp. 647-668, 1988.

* cited by examiner

US 7,022,340 B2

PHARMACEUTICAL COMPOSITION AS SOLID DOSAGE FORM AND METHOD FOR MANUFACTURING THEREOF

FIELD OF THE INVENTION

The present invention relates to a novel pharmaceutical composition as a solid dosage form comprising desmopressin as a therapeutically active ingredient, and to a method for manufacturing thereof.

TECHNICAL BACKGROUND

Desmopressin, also known as dDAVP, is the therapeutically active ingredient (as its acetate salt) in the pharmaceutical product Minirin®, which is marketed inter alia as a nasal spray and a tablet formulation. Desmopressin is primarily used in the treatment of primary nocturnal enuresis, i.e. bedwetting, in children, but it is approved also for the treatment of nocturia and diabetes insipidus. The first market introduction of the tablet formulation was in Sweden in 1987.

In short, a solid dosage form such as a tablet formulation is typically manufactured by compression of a suitable granulate to the desired solid dosage form, where the granulate is composed of the required constituents as a mixture of solid particles. Typical such particles are the therapeutically active ingredient, various excipients, disintegrating agents, lubricants and binders, optionally together e.g. with flavoring agent, preservative and/or colorant. The commercially available Minirin® tablet is prepared according to this general protocol, and the tablet was first disclosed as set forth in the patent U.S. Pat. No. 5,047,398, the teachings of which are incorporated herein by reference. For a comprehensive overview of pharmaceutical tablet manufacturing, see "Tableting" (by N. A. Armstrong) in "Pharmaceutics— The science of dosage form design", pp 647–668; Ed. M. E. Aulton, Churchill Livingstone, Edinburgh, London, Melbourne and New York, 1988, the entire teachings of which are incorporated herein by reference.

The Minirin® tablet that is currently marketed, and thus produced in industrial scale, consists of the therapeutically active ingredient desmopressin together with potato starch and lactose as excipients, and a suitable, amount of hinder and lubricant, respectively.

When preparing tablets, there is a general desire to obtain tablets that are as hard as possible (e.g. to reduce attrition in storage and handling) while avoiding detrimental effects on pharmaceutical properties such as disintegration time and drug release profile within the gastrointestinal tract. Moreover, a tablet should not be made so hard that it can not be chewed without, teeth damaging or otherwise excessive effort. If the tablets are prepared by compression of a granulate or a powder, additional care must also be taken to optimise the desired hardness in order to minimise machine wear and at the same time perform the compressing operation at the highest possible speed. Furthermore, in compressing operations one has to overcome the, problem that increased compression speed inherently tends to reduce the maximum attainable hardness.

In a compressing operation in a typical tabletting machinery, the tablets resulting from the compression of a granulate are ejected from the die in which they have been prepared by a punch, and the arising friction between the tablet and the die walls may thereby be considerable. Such friction may lead to an increased frequency of tablet rupture, i.e. in effect a waste of tablets, and also to increased wear of the tabletting machinery in general. It is therefore developed practice in the art to reduce the aforementioned friction by adding lubricant to powder or granulate that is to be compressed. For this purpose, a lubricant (magnesium stearate) is and has been present in the commercial Minirin® tablet in an amount of 0.50 percent by weight of the tablet.

DISCLOSURE OF THE INVENTION

Figure 1:
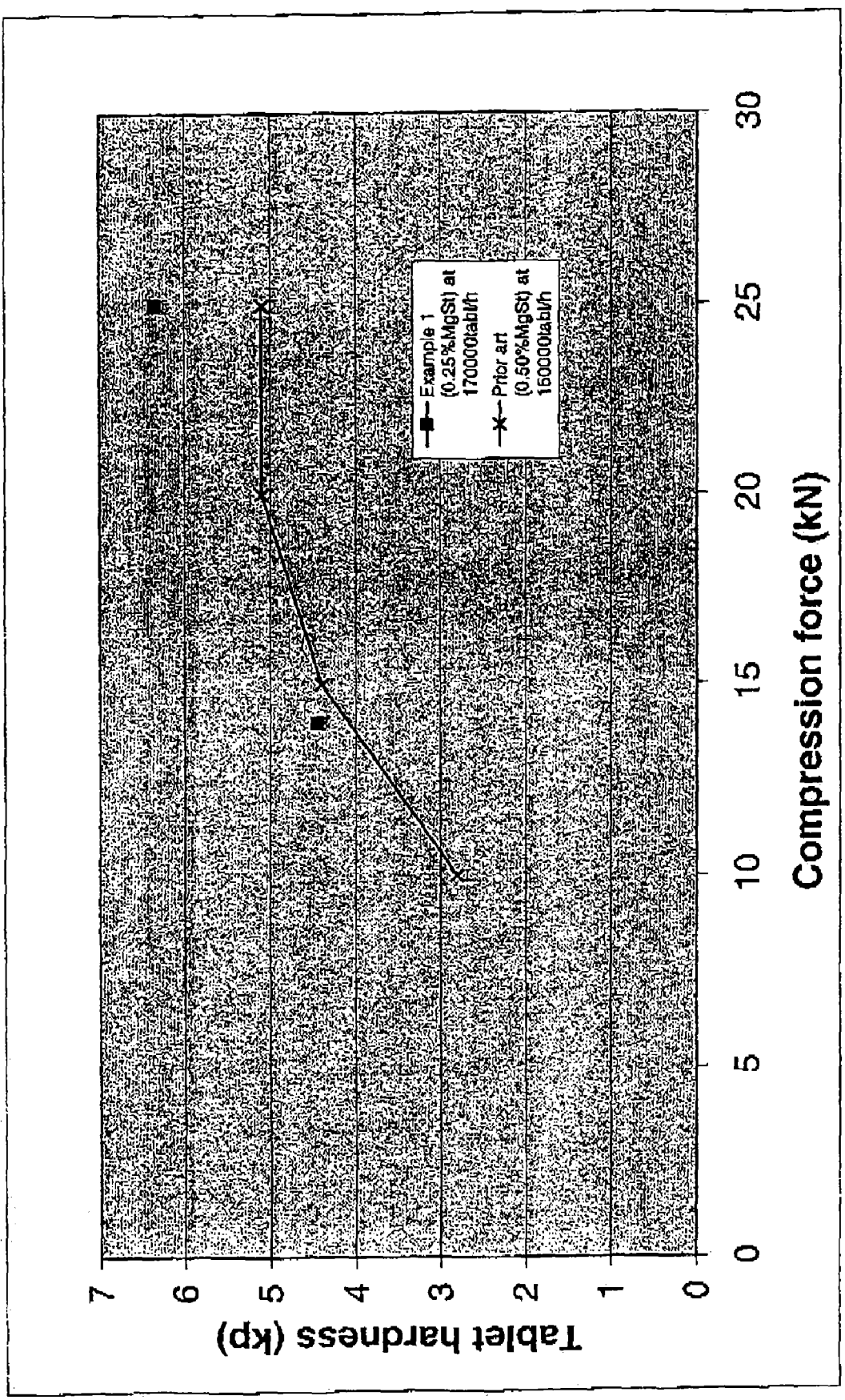
FIG. 1 illustrates the attainable hardness and compressing speed into tablets for the present invention compared to that of the prior art granulate.

The problem of obtaining the desired hardness, including convenient control thereof, in balance with the other aforementioned considerations is successfully addressed in the present invention by the discovery of a purposive lowering of the amount of lubricant in a solid dosage form comprising desmopressin. By practising the present invention increased hardness in combination with increased compressing speed is also attainable. More specifically, the present invention relates to a pharmaceutical composition as a solid dosage form comprising desmopressin, or a pharmaceutically acceptable salt thereof, as a therapeutically active ingredient together with a pharmaceutically acceptable excipient, diluent or carrier, or mixture thereof, wherein the pharmaceutical composition is composed of a compressed granulate and contains lubricant in an amount of from 0.05 to less than 0.50 percent by weight of said pharmaceutical composition.

Percent by weight relates to the resulting percentage of the weight of the final pharmaceutical composition.

In many cases the terms excipient, diluent and carrier can be used interchangeably, and they may even refer to one and the same substance, or to a mixture of similar such substances. The proper use and understanding of these terms is self-explanatory and lies well within the ability of a person skilled in the art of pharmaceutical formulation.

In a preferred embodiment, said pharmaceutical composition contains lubricant in an amount of from 0.10 to less than 0.50 percent by weight of said pharmaceutical composition. In an even more preferred, embodiment, said pharmaceutical composition contains lubricant in an amount of from 0.15 to 0.45, preferably from 0.20 to 0.40, and more preferably from 0.25 to 0.30, percent by weight of said pharmaceutical composition.

It is preferred that said compressed granulate has an average size of a least 100 μm, preferably in the range of from 100 μm to 2 mm, more preferably in the range of from 100 to 600 μm.

It is particularly preferred that said granulate has a size distribution where at least 50%, preferably from 50 to 90%, by volume thereof consists of granulate particles with a size of at least 100 μm, preferably, in the range of from 100 μm to 2 mm, more preferably, in the range of from 100 to 600 μm. It deserves mentioning that the granulate compressed into the present commercially available tablet has a size distribution where more than 50% by volume thereof consists of granulate particles, with a size of less than 100 μm (cf. FIG. 2). The size distribution as provided herein is measured by conventional laser diffraction technique by using a Mastersizer 2000 provided by Malvern Instruments Ltd. The laser diffraction technique is described in "Particle Size MeasuremLent", 5th Ed., pp 392–448, vol. 1; T. Allen, Chapman & Hall, London, UK, 1997.

Said lubricant is typically selected from a group consisting of stearic acid, salts or esters of stearic acid, hydrogenated vegetable oils magnesium oxide, polyethylene glycol, sodium lauryl sulphate and talc, and mixtures thereof. Preferably said lubricant is selected from magnesium stearate, calcium stearate, zinc stearate, glyceryl palmitostearate and sodium stearyl fumarate, and mixtures thereof. Magnesium stearate is the most preferred alternative.

In a particularly preferred embodiment, at least one of said excipient, diluent and carrier is a substance selected from a monosaccharide, disaccharide, oligosaccharide and a polysaccharide. Preferably the said substance has an average particle size in the range of from 60 to 1000 μm. As outlined below, this embodiment is particularly advantageous, and where there is a mixture of at least two of the aforementioned types of saccharides, at least one of them is accordingly within the said particle-size range.

The pharmaceutical composition according to the present invention may optionally comprise at least one additive selected from a disintegrating agent, binder, flavoring agent, preservative, colorant and a mixture thereof. Where considered suitable also other additives may be included. Representative examples of disintegrating agents, binders (e.g. Kollidon® 25, BASF), flavoring agents, preservatives and colorants, and suitable mixtures thereof, as well as any other conventional additive that may be considered by a person skilled in the art practising the present invention, can be found in "*Handbook of Pharmaceutical Excipients*"; Ed. A. H. Kibbe, 3rd Ed., American Pharmaceutical Association, USA and Pharmaceutical Press UK, 2000, the teachings of which are incorporated herein by reference. As an example, also applicable in the practising of the present invention, it can be mentioned that a typical amount of binder is in the order of less than 6 percent by weight of the pharmaceutical composition.

As used herein, the expression oligosaccharide relates to a chain, with any degree of branching, of from three to ten monosaccharide units linked via glycoside bonds. Accordingly, as used herein, the expression polysaccharide relates to a chain, with any degree of branching, of at least eleven monosaccharide units linked via glycoside bonds. Synthetically modified derivatives and analogues of naturally occurring saccharides are also possible to use in the practising of the present invention.

In the marketed tablet resulting from the hitherto used manufacturing process, the lactose particles (Pharmatose® 150M provided by DMV, the Netherlands) that are incorporated into the formed granulate have an average size of about 50 μm, as determined by an air jet sieve (provided by Alpine GmbH, DE). That particle size does not provide a granulate that allows a compressing speed exceeding about 170 000 tablets per hour (h). Indeed, in the most preferred embodiment of the present invention, hence also including the aforementioned particle size range (vide infra), a compressing speed of up to about 250 000 tablets/h with the desired tablet quality and retained low level of wear on the tabletting machinery is attainable.

As further examples of an upper limit for said average particle size mention can be made of 900, 800, 700 and 600 μm. In a preferred embodiment said average particle size is in the range of from 70 to 500 μm. In another preferred embodiment, said average particle size is in the range of from 75 to 350 μm. In yet another preferred embodiment, said average particle size is in the range of from 100 to 200 μm. In a further preferred embodiment, said average particle size is in the range of from 120 to 180 μm. In the most preferred embodiment of the present invention, said average particle size is 140 μm (as measured by an air jet sieve). The lactose particles sold as Pharmatose® DCL 15, marketed by DMV in the Netherlands, are of this most preferred average particle size. Other particular embodiments may involve use of e.g. Pharmatose® DCL 11, Pharmatose® DCL 21 and Pharmatose® DCL 40, all provided by the aforementioned DMV, which have an average particle size of 110, 150 and 165 μm, respectively. Other examples are the Tablettase® 70, 80 and 100 series provided by Meggle AG, DE.

According to the commercial provider the particle size distribution of Pharmatose® DCL 15 is that essentially all particles have a size below 500 μm, whereas approximately 72% of the particles have a size of from 75 to 350 μm.

In an air jet sieve measurement of particle size, air is drawn upwards, through a sieve, from a rotating slit so that material on the sieve is fluidised. At the same time a negative pressure is applied to the bottom of the sieve which removes fine particles to a collecting device. Size analyses and determination of average particle size are performed by removal of particles from the fine end of the size distribution by using single sieves consecutively. See also "*Particle Size Measurement*", 5th Ed., p 178, vol. 1; T. Allen, Chapman & Hall, London, UK, 1997, for more details on this. For a person skilled in the art, the size measurement as such is thus of conventional character.

Accordingly, it is preferred that said substance is a disaccharide, preferably lactose, and more preferably lactose-α-monohydrate.

As said polysaccharide, starch is preferred, and of the many available starches, potato starch is the most preferred. Ad examples of potato starches mention can be made of Pharma M20, Pharma M14 (provided by KMC, DK) and AmylSolVät (provided by Lyckeby Starkelse AD, SE).

In a preferred embodiment, both said disaccharide and polysaccharide are present in the pharmaceutical composition. In that particular embodiment, the weight ratio between said disaccharide and polysaccharide is typically from 100:1 to 1:100, preferably from 10:1 to. 1:10, and more preferably from 2:1 to 1:2.

The total combined amount of said excipient, diluent and carrier is usually from 5 to 99, preferably from 50 to 99, percent by weight of the pharmaceutical composition, the balance up to 100% being the therapeutically active ingredient and lubricant optionally together with the aforementioned additives. The latter is preferably a binder.

The pharmaceutical composition as a solid dosage form according to the present invention is typically a perorally available tablet. As an alternative non-limiting embodiment, the said tablet may be adapted for oral, including buccal and/or sublingual administration.

The composition typically comprises desmopressin acetate in an amount of from 20 to 600 μg per unit of solid dosage form. As an example, a typical tablet containing 100 μg of desmopressin acetate is white, convex and oval (6.7×9.5 mm) with a thickness of 3–4 mm and a weight of 200 mg. As another example, a tablet containing 200 μg of desmopressin acetate is white, round (8 mm diameter) and convex with a thickness of 3–4 mm and a weight of 200 mg.

In a preferred embodiment, each unit of solid dosage form has a hardness of at least 5 kp (1 kp=9.81 N) typically with 7 kp as the practical upper limit. As demonstrated in the experimental part (cf. FIG. 1), a tablet hardness exceeding 6 kp is possible with the present invention, and such hardness was not achievable with the prior art tablet. The hardness test of Minirin® tablets is performed by measuring the force needed to disrupt the tablets by crushing, using a conventional tablet hardness tester.

Accordingly, a further aspect of the present invention relates to a method for the manufacturing of a pharmaceutical composition as a solid dosage form comprising desmopressin, or a pharmaceutically acceptable salt thereof, as a therapeutically active ingredient, wherein said method comprises the steps of:

i) mixing desmopressin and an excipient, diluent or carrier, or mixture thereof, optionally in the presence of a wetting agent;

ii) subjecting the resulting mixture to formation of a granulate, optionally in the presence of a wetting agent, suitable for compression into said solid dosage form;

iii) optionally performing said mixing and/or formation of a granulate in the presence of at least one additive selected from a disintegrating agent, binder, flavoring agent, preservative, colorant and a mixture thereof;

iv) optionally drying said granulate;

v) compressing said granulate into said solid dosage form;

wherein lubricant is introduced so that the resulting pharmaceutical composition contains lubricant in an amount of from 0.05 to less than 0.50 percent by weight of said pharmaceutical composition. Said lubricant is usually introduced before the compressing operation of step v), and preferably immediately after granulate formation, after granulate drying, where relevant.

The method according to the present invention can as such, once the specific components are identified and included, be practised by using conventional equipment for the manufacturing of pharmaceutical formulations. A granulate suitable for compression into tablets typically has an average granulate size of at least about 100 μm. Discrete granules with a size above 2 mm are usually not transferred to the subsequent compressing step.

As non-limiting examples mention can be made of the following equipment for granulation: directly heated fluidised solid beds e.g. provided by GEA/Collette NV, BE (UltimaPro™ series), Hüttlin GmbH, DE (HDG series), Diosna Dierks & Soehne GmbH, DE (VAC series), Fluid Air Inc., US (Magnaflo® series) and Vector Corp., US (GMX series); indirect conduction moving solids bed, including paddle systems, rotary systems and agitation systems, which are e.g. provided by Jaygo Inc., US (JRB and Novamix series), Paul O. Abbé Inc., US (Rota-Cone, Rota-U, Rota Blade, Cylindrical Ribbon/Paddle, Plow and Sigma-blade series), Forberg A/S, No (Forberg II series), Gemco Inc. US (D/3 Double Cone, V-Shape and Slant-Cone series), LittlefordDay Inc., US (Double Arm, Day Nauta and Daymax series), Patterson-Kelly, Harsco Corp., US (P-K solids Processor® series), Diosna as above (CCS and VAC series), Romaco Zanchetta SpA, IT (Roto E, Roto D and Roto P series) and L. B. Bohle Maschinen und Verfahren GmbH, DE (Granumator GMA and Vagumator VMA series). The aforementioned equipment in general also provides drying of the prepared granules.

In a preferred embodiment of the method the pharmaceutical composition will contain lubricant in an amount of from 0.10 to less than 0.50 percent by weight. In an even more preferred embodiment, the pharmaceutical composition will contain lubricant in an amount of from 0.15 to 0.45, preferably from 0.20 to 0.40, and more preferably from 0.25 to 0.30, percent by weight.

It is preferred that said resulting mixture is subjected to formation of a granulate with an average size of a least 100 μm; preferably in the range of from 100 μm to 2 mm, more preferably in the range of from 100 to 600 μm.

It is particularly preferred that said formation of granulate provides a size distribution where at least 50%, preferably from 50 to 90%, by volume of said granulate consists of granulate particles with a size of at least 100 μm, preferably in the range of from 100 μm to 2 mm, more preferably in the range of from 100 to 600 μm. The size distribution is measured as set forth above.

In the method, said lubricant is typically selected from the aforementioned group of compounds, including mixtures thereof. Magnesium stearate is the most preferred lubricant.

In an especially preferred embodiment of the method of the invention, at least one of said excipient, diluent and carrier is a substance selected from a monosaccharide, disaccharide, oligosaccharide and a polysaccharide. Preferably said substance has an average particle size in the range of from 60 to 1 000 μm.

As indicated above, further examples of an upper limit for said average particle size are 900, 800, 700 and 600 μm. It is preferred that said average particle size is in the range of from 70 to 500 μm. In another preferred embodiment, said average particle size is in the range of from 75 to 350 μm. In yet another preferred embodiment, said average particle size is in the range of from 100 to 200 μm. In a further preferred embodiment, said average particle size is in the range of from 120 to 180 μm. In the most preferred embodiment of the present invention, said average particle size is 140 μm. The lactose particles sold as Pharmatose® DCL 15, marketed by DMV in the Netherlands, are of this most preferred average particle size. Other possible embodiments of the present method may involve the aforementioned variants of Pharmatose® DCL and Tablettose® (vide supra).

It is accordingly preferred that said substance is a disaccharide, preferably lactose, and more preferably lactose-α-monohydrate. Said monosaccharide may also be D-mannitol, D-sorbitol or xylitol or a mixture thereof.

Said polysaccharide is preferably a starch, and more preferably potato starch. Preferred particular potato starches are the same as set forth above.

In the method according to the present invention, the manufactured solid dosage form is typically a perorally available tablet. Where desired, it may also be in a form and/or composition adapted for oromucosal administration. Preferred examples of the latter are buccal and/or sublingual administration. Examples of tablet compressing equipment suitable for the practising of the present invention are rotary presses provided by Elizabeth-Hata International, US (HT series), Courtoy NV, BE (R090F, R100M, R190FT, R290FT, R292F and R233 series), Vector Corp., US (2000, 200 and Magna series), Fette GmbH, DE (Hightech, Medium, Special and WIP series), Manesty, UK (Xpress, Diamond and Value series) and Kilian & Co. GmbH, DE (S, T, E, RX and KTS series).

In a preferred embodiment of the present inventive method said steps of mixing and formation of granulate are performed in a single integrated machinery that is adapted for such a "one-pot", i.e. combined, process. An example of such integrated machinery, alternatively denoted one-pot (single pot) equipment, is the FT series, provided by Forberg A/S, Norway.

It is preferred that where used, said wetting agent is selected from water and a mixture of water and an alcohol, preferably ethanol. A water/ethanol 1:3 mixture is typically used, albeit many other combinations are also possible.

It is preferred that both said disaccharide and polysaccharide are present in the mixing step. The weight ratio between said disaccharide and polysaccharide is then typically from 100:1 to 1:100, preferably from 10:1 to 1:10, and more preferably from 2:1 to 1:2.

The method is preferably performed in such a manner that the total combined amount of said excipient, diluent and carrier is from 5 to 99, preferably from 50 to 99, percent by weight of the pharmaceutical composition.

In the most preferred embodiment, desmopressin acetate is used and mixed with said excipient, diluent and/or carrier in an amount that eventually provides from 20 to 600 μg of desmopressin acetate per unit of solid dosage form (see above and the experimental part for examples of a tablet).

The granulate forming each unit of solid dosage form is preferably compressed to a hardness of at least 5 kp. The experimental part (cf. FIG. 1) illustrates that a tablet hardness exceeding 6 kp is possible with the present invention. As indicated above, such hardness was not achievable by compression of the prior art granulate.

In a further aspect, the present invention also relates to a pharmaceutical composition as a solid dosage form that is obtainable by the novel method as defined above, both in general and as outlined in the specific embodiments.

In order to substantiate and illustrate the present invention in more detail, the following example is provided. It shall not be construed as a limitation of how the invention may be practised.

EXAMPLE

Example 1

Preparation of Tablet Form of dDAVP

Desmopressin acetate (100 or 200 g; provided by PolyPeptide Laboratories AB, SE), polyvinyl pyrrolidone (PVP) as binder (1,9 kg; Kollidon® 25 provided by BASF GmbH, DE) and granulation liquid (water/ethanol 1:3 mixture) are combined in a vessel and mixed at room temperature until a clear solution is achieved. Potato starch (73.4 kg, average particle size about 40–50 μm according to laser diffraction measurements; AmylSolVät provided by Lyckeby Starkelse AB, SE), is weighed and sieved through a 2 mm sieve. Lactose (123.7 kg, DCL 15 provided by DMV NV, NL; see above for the details of this product) is weighed and loaded tog ether with the starch into a single pot mixer (FT-350, provided by Forberg A/S, NO) and mixed therein, The granulation liquid solution is then sprayed onto the powder mixture, after which the moist granulate is dried with warm air (150° C.), all with continued mixing. The dried granulate is then sieved (2 mm) and transferred to a double cone mixer. Magnesium stearate (0.51 kg; provided by Peter Graven NV, NL; equal to 0.25% by weight of the final tablet) is then weighed in, sieved (1 mm) and transferred to the double cone mixer for final mixing. Tablets are then compressed from the resulting mixture by using a conventional rotary tablet compression machine (Kilian S-250).

Several compressing operations measuring attainable tablet hardness as a function of compaction force at similar compressing speeds were performed with the above type of granulate and compared with a granulate containing 0.50% by weight of magnesium stearate. The latter granulate had the size distribution of more than 50% by volume thereof being granulate particles with a size of less than 100 μm. The results depicted in FIG. 1 clearly show that the granulate according to the present invention can provide a harder tablet compared to the prior art granulate.

Figure 2:
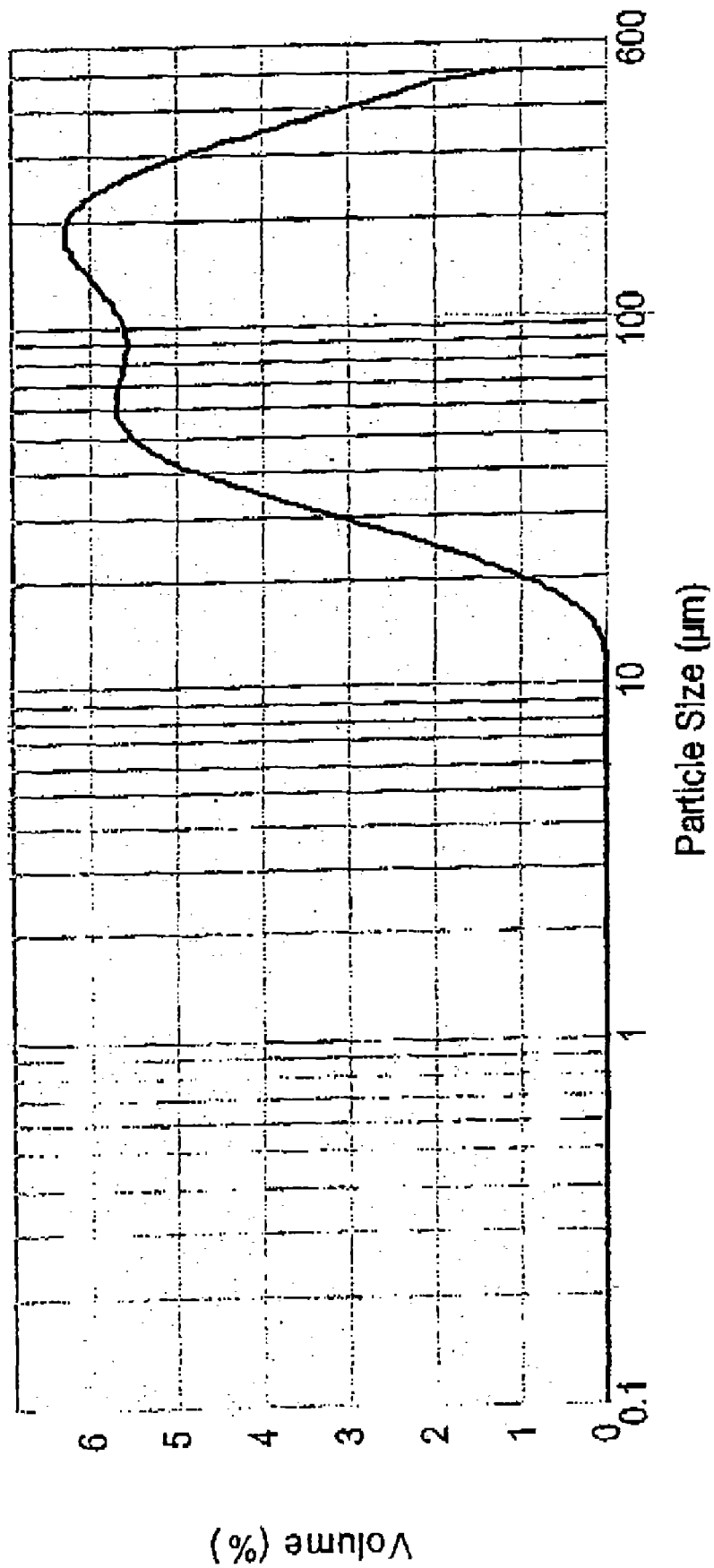
FIG. 2 illustrates in detail the size distribution pattern of the granulate prepared in example 1.

The size distribution of the above granulate is depicted in detail in FIG. 2, and the measurement is performed in a Mastersizer as set forth above.

In the particular embodiment of granulate set forth in this example, a granulate compressing speed of about 250 000 tablets/h is attainable with adequate tablet quality and low machine wear. A tablet of adequate quality has a smooth surface without scratches or chipped edges, and it shows no tendencies to lamination (so-called capping).

The process is typically adapted to provide a tablet containing 100 or 200 μg of desmopressin acetate with the aforementioned appearance, dimension and weight.

The invention claimed is:

1. A pharmaceutical composition as a tablet, comprising desmopressin acetate, as a therapeutically active ingredient together with a pharmaceutically acceptable excipient, diluent or carrier, or mixture thereof, wherein the pharmaceutical composition is composed of a compressed granulate and contains lubricant in an amount of from 0.05 to 0.40 percent by weight of said pharmaceutical composition, and wherein said tablet comprises from 20 to 600 μg desmopressin acetate.

2. A pharmaceutical composition according to claim 1 which contains lubricant in an amount of from 0.10 to 0.30 percent by weight of said pharmaceutical composition.

3. A pharmaceutical composition according to claim 2 which contains lubricant in an amount of from 0.15 to 0.30 percent by weight of said pharmaceutical composition.

4. A pharmaceutical composition according to claim 1 which is composed of a compressed granulate with an average size of at least 100 μm.

5. A pharmaceutical composition according to claim 4, wherein said granulate has a size distribution where at least 50% by volume thereof consists of granulate particles with a size of at least 100 μm.

6. A pharmaceutical composition according to claim 1, wherein said lubricant is selected from a group consisting of stearic acid, salts or esters of stearic acid, hydrogenated vegetable oils, magnesium oxide, polyethylene glycol, sodium lauryl sulphate and talc, and mixtures thereof.

7. A pharmaceutical composition according to claim 6, wherein said lubricant is selected from magnesium stearate, calcium stearate, zinc stearate, glyceryl palmitostearate and sodium stearyl fumarate, and mixtures thereof.

8. A pharmaceutical composition according to claim 1, wherein at least one of said excipient, diluent and carrier is a substance selected from a monosaccharide, disaccharide, oligosaccharide and a polysaccharide.

9. A pharmaceutical composition according to claim 8, wherein the said substance has an average particle size in the range of from 60 to 1000 μm.

10. A pharmaceutical composition according to claim 9, wherein said average particle size is in the range of from 70 to 500 μm.

11. A pharmaceutical composition according to claim 8, wherein said substance is a disaccharide.

12. A pharmaceutical composition according to claim 8, wherein said polysaccharide is a starch.

13. A pharmaceutical composition according to claim 8, wherein both said disaccharide and polysaccharide are present.

14. A pharmaceutical composition according to claim 13, wherein the weight ratio between said disaccharide and polysaccharide is from 100:1 to 1:100.

15. A pharmaceutical composition according to claim 1, wherein the total combined amount of said excipient, diluent and carrier is from 5 to 99 percent by weight of the pharmaceutical composition.

16. A pharmaceutical composition according to claim 1, wherein said tablet is a perorally available tablet that is optionally adapted for oromucosal administration.

17. A pharmaceutical composition according to claim 1, wherein each unit of tablet has a hardness of at least 49N (5 kp).

18. A method for the manufacturing of a pharmaceutical composition as a tablet comprising desmopressin acetate as a therapeutically active ingredient, wherein said method comprises the steps of:
   i) mixing desmopressin acetate, and an excipient, diluent or carrier, or mixture thereof, optionally in the presence of a wetting agent, in an amount that provides from 20 to 600 µg of desmopressin acetate per tablet;
   ii) subjecting the resulting mixture to formation of a granulate, optionally in the presence of a wetting agent, suitable for compression into said tablet;
   iii) optionally performing said mixing and/or formation of a granulate in the presence of at least one additive selected from a disintegrating agent, binder, flavoring agent, preservative, colorant and a mixture thereof;
   iv) optionally drying said granulate;
   v) compressing said granulate into said tablet,
   wherein lubricant is introduced so that the resulting pharmaceutical composition contains lubricant in an amount of from 0.05 to 0.40 percent by weight of said pharmaceutical composition.

19. A method according to claim 18, wherein the pharmaceutical composition contains lubricant in an amount of from 0.10 to 0.30 percent by weight of said pharmaceutical composition.

20. A method according to claim 19, wherein the pharmaceutical composition contains lubricant in an amount of from 0.15 to 0.30 percent by weight of said pharmaceutical composition.

21. A method according to claim 18, wherein said resulting mixture is subjected to formation of a granulate with an average size of at least 100 µm.

22. A method according to claim 21, wherein said formation of granulate provides a size distribution where at least 50% by volume of said granulate consists of granulate particles with a size of at least 100 µm.

23. A method according to claim 18, wherein said lubricant is selected from a group consisting of stearic acid, salts or esters of stearic acid, hydrogenated vegetable oils, magnesium oxide, polyethylene glycol, sodium lauryl sulphate and talc, and mixtures thereof.

24. A method according to claim 23, wherein said lubricant is selected from magnesium stearate, calcium stearate, glyceryl palmitostearate, sodium stearyl fumarate and zinc stearate, and mixtures thereof.

25. A method according to claim 18, wherein at least one of said excipient, diluent and carrier is a substance selected from a monosaccharide, disaccharide, oligosaccharide and a polysaccharide.

26. A method according to claim 25, wherein said substance has an average particle size in the range of from 60 to 1000 µm.

27. A method according to claim 26, wherein said average particle size is in the range of from 70 to 500 µm.

28. A method according to claim 25, wherein said substance is a disaccharide.

29. A method according to claim 25, wherein said polysaccharide is a starch.

30. A method according to claim 18, wherein said tablet is a perorally available tablet that is optionally adapted for oromucosal-administration.

31. A method according to claim 18, wherein said wetting agent is selected from water and a mixture of water and an alcohol.

32. A method according to claim 18, wherein both said disaccharide and polysaccharide are present in the mixing step.

33. A method according to claim 32, wherein the weight ratio between said disaccharide and polysaccharide is from 100:1 to 1:100.

34. A method according to claim 18, wherein the total combined amount of said excipient, diluent and carrier is from 5 to 99 percent by weight of the pharmaceutical composition.

35. A pharmaceutical composition according to claim 4 wherein said granulate has an average size of from 100 to 600 µm.

36. A pharmaceutical composition according to claim 5, wherein said granulate has a size distribution where from 50 to 90% by volume thereof consists of granulate particles with a size of at least 100 µm.

37. A pharmaceutical composition according to claim 5, wherein said granulate has a size distribution where at least 50% by volume thereof consists of granulate particles with a size in the range of from 100 to 600 µm.

38. A pharmaceutical composition according to claim 10, wherein said average particle size is in the range of from 100 to 200 µm.

39. A pharmaceutical composition according to claim 10, wherein said average particle size is in the range of from 120 to 180 µm.

40. A pharmaceutical composition according to claim 11, wherein said substance is lactose-α-monohydrate.

41. A pharmaceutical composition according to claim 12, wherein said polysaccharide is a potato starch.

42. A pharmaceutical composition according to claim 14, wherein the weight ratio between said disaccharide and polysaccharide is from 2:1 to 1:2.

43. A pharmaceutical composition according to claim 15, wherein the total combined amount of said excipient, diluent and carrier is from 50 to 99 percent by weight of the pharmaceutical composition.

44. A pharmaceutical composition according to claim 16, wherein said tablet is a perorally available tablet that is optionally adapted for buccal and/or sublingual administration.

45. A method according to claim 21, wherein said resulting mixture is subjected to formation of a granulate with an average size of a from 100 to 600 µm.

46. A method according to claim 22, wherein said formation of granulate provides a size distribution where from 50 to 90% by volume of said granulate consists of granulate particles with a size of at least 100 µm.

47. A method according to claim 22, wherein said formation of granulate provides a size distribution where at least 50% by volume of said granulate consists of granulate particles with a size in the range of from 100 to 600 µm.

48. A method according to claim 27, wherein said average particle size is in the range of from 100 to 200 µm.

49. A method according to claim 27, wherein said average particle size is in the range of from 120 to 180 µm.

50. A method according to claim 28, wherein said substance is lactose-α-monohydrate.

51. A method according to claim 29, wherein said polysaccharide is a potato starch.

52. A method according to claim 30, wherein said tablet is a perorally available tablet that is optionally adapted for buccal and/or sublingual administration.

53. A method according to claim 31, wherein said alcohol is ethanol.

54. A method according to claim 33, wherein the weight ratio between said disaccharide and polysaccharide is from 2:1 to 1:2.

55. A method according to claim 18, wherein the total combined amount of said excipient, diluent and carrier is from 50 to 99 percent by weight of the pharmaceutical composition.

* * * * *